(12) United States Patent
Schoening et al.

(10) Patent No.: US 8,519,360 B2
(45) Date of Patent: Aug. 27, 2013

(54) METHOD AND APPARATUS FOR DISINFECTION VERIFICATION

(75) Inventors: Brian Schoening, Hanover Park, IL (US); Troy Grow, North Chicago, IL (US)

(73) Assignee: BOS Innovations Ltd., Grayslake, IL (US)

( * ) Notice: Subject to any disclaimer, the term of this patent is extended or adjusted under 35 U.S.C. 154(b) by 277 days.

(21) Appl. No.: 13/036,837

(22) Filed: Feb. 28, 2011

(65) Prior Publication Data

US 2012/0217417 A1    Aug. 30, 2012

(51) Int. Cl.
*G01N 21/64* (2006.01)

(52) U.S. Cl.
USPC ...................................... 250/461.1

(58) Field of Classification Search
USPC ............... 250/301, 302, 458.1, 459.1, 365, 250/372, 461.1
See application file for complete search history.

(56) References Cited

U.S. PATENT DOCUMENTS

| | | | | |
|---|---|---|---|---|
| 6,476,385 | B1 * | 11/2002 | Albert | 250/302 |
| 7,718,395 | B2 * | 5/2010 | Carling | 435/36 |
| 7,780,453 | B2 * | 8/2010 | Carling | 434/365 |
| 7,785,109 | B2 * | 8/2010 | Carling | 434/370 |
| 8,084,410 | B2 * | 12/2011 | Carling | 510/161 |
| 2003/0197122 | A1 * | 10/2003 | Faiola et al. | 250/302 |
| 2006/0218987 | A1 * | 10/2006 | Campman | 73/23.2 |
| 2009/0042757 | A1 * | 2/2009 | Carling | 510/100 |

OTHER PUBLICATIONS

Alice Guh, MD, MPH; Philip Carling, MD; Environmental Evaluation Workgroup, "Options for Evaluating Environmental Cleaning," Centers for Disease Control and Prevention, Oct. 2010, 15 pages.
"Glow Testing Systems—Environmental Forensic Testing," Kaiser Permanente, undated but believed to be published at least as early as Dec. 15, 2010, 12 pages.
"Glow Testing System—A Focus on Health and Disease Prevention," Kaiser Permanente, undated but believed to be published as early as Dec. 15, 2010, 24 pages.
INVIS-ID [online]. [retrieved on Feb. 8, 2011]. Retrieved from the Internet: <http://www.conceptek.com/business-php>, 1 page.

* cited by examiner

*Primary Examiner* — Mark R Gaworecki
(74) *Attorney, Agent, or Firm* — Neal Gerber & Eisenberg, LLP

(57) ABSTRACT

A method and a kit for verifying whether a surface has been cleaned or disinfected comprising marking one or more inanimate surfaces with an invisible solution, such as an ink, prior to cleaning or disinfection of the surface, and after cleaning or disinfection of the surface is purportedly completed, using an ultraviolet light source to illuminate any ink not removed in the cleaning and disinfection process. The invisible solution may be easily cleaned or removed from the one or more surfaces by, for example, washing or wiping with, for example, soap and water. A kit includes a marking device containing a liquid compound which is made visible when exposed to ultraviolet light, and a light source which, when illuminating a surface that has been marked with the liquid compound, fluoresces or otherwise makes visible any of the compound remaining on the surface following cleaning or disinfection operations.

8 Claims, 2 Drawing Sheets

METHOD AND APPARATUS FOR DISINFECTION VERIFICATION

BACKGROUND OF THE INVENTION

Proper cleaning and disinfection of surfaces is essential to the health of patients and employees in sterile environments, such as hospitals, health clinics and dental offices, and of users of other public locations such as, for example, offices, schools, hotels, restaurants, airports, train stations and taxis, to name a few. In many situations, it may be difficult to ascertain after the fact whether one or more target areas of a surface has been cleaned. And while visual inspection provides an indication of the cleanliness of a surface, human eyes alone are not able to detect whether cleaning personnel actually cleaned or disinfected a surface. In addition, testing surfaces for the absence of dirt or organisms, is costly, requires specialized testing equipment, and often requires considerable time to perform. As such, a fast, simple, cost-effective method of determining whether one or more target areas of a surface have been cleaned would be helpful.

SUMMARY OF THE INVENTION

A method and apparatus is disclosed for verifying whether a surface has been cleaned or disinfected. In one embodiment, the method comprises marking one or more inanimate surfaces with an invisible solution, such as an ink, prior to cleaning or disinfection of the surface, and after cleaning or disinfection of the surface is purportedly completed, using an ultraviolet light source to illuminate any ink not removed in the cleaning and disinfection process. The invisible solution may be easily cleaned or removed from the one or more surfaces by, for example, washing or wiping with, for example, soap and water, or organic or inorganic emulsifiers, detergents, abrasives, and chemical agents. In another embodiment, an apparatus for verifying the cleanliness or disinfection of one or more surfaces comprises a kit having a marking device containing an ink solution which is made visible when exposed to ultraviolet light, and a light source which, when illuminating a surface that has been marked with the ink solution, fluoresces or otherwise makes visible any ink remaining on the surface following cleaning or disinfection operations.

DETAILED DESCRIPTION

Figure 1:
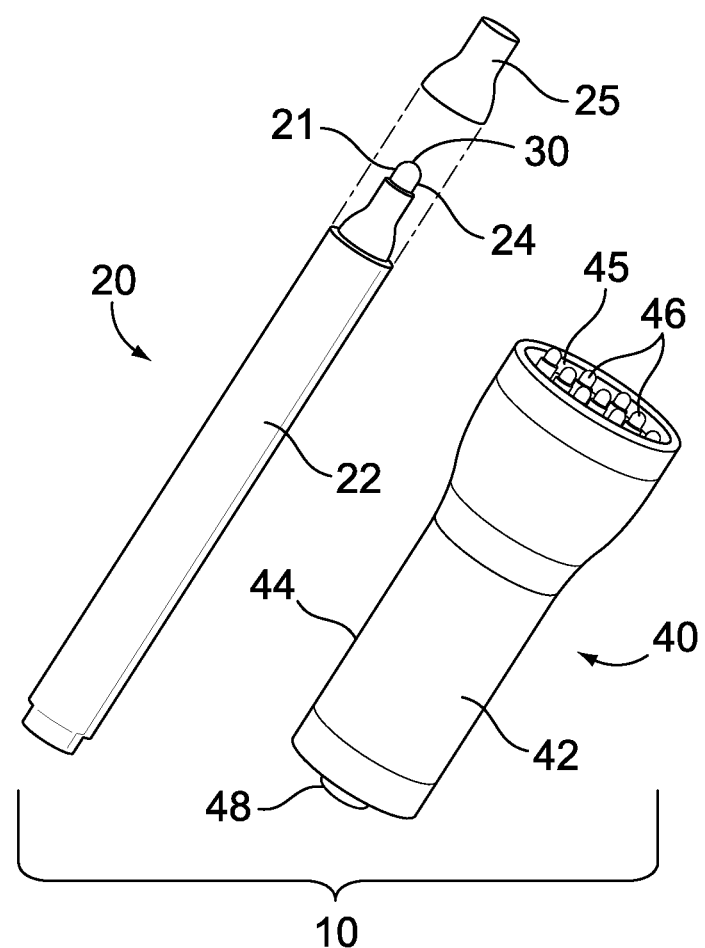
FIG. 1 is front perspective view of an exemplary kit for cleaning or disinfection verification in accordance with one embodiment of the present invention.

Turning now to the figures, wherein like reference numerals refer to like elements, there is illustrated in FIG. 1 an exemplary cleaning and disinfection verification kit 10 comprising marking device 20 and light source 40. In one embodiment, marking device 20 is a portable, handheld marker-type device which comprises body 22 and applicator 21 having tip 24 for dispensing liquid compound 30, such as an ink, onto one or more surfaces to be cleaned or disinfected and thereafter verified in accordance with the teachings of the instant disclosure. Applicator 21 comprises a felt, a sponge, or other similar material capable of absorbing and dispensing liquid compound 30. Applicator 21 may have an elongated portion (not shown) emersed in a reservoir (not shown) inside body 22 of marking device 20 from which liquid compound 30 may be drawn to moisten tip 24. Marking device 20 may also include cap 25 that removably engages with body 22 for placement over tip 24 of applicator 21 to prevent leaking or drying of liquid compound 30 therein. Cap 25 may snap into place on body 22 over tip 24 to protect tip 24 and liquid compound 30 from drying. A suitable marking device 20 is available from Specialty Ink Company, Inc. in Deer Park, N.Y. In another embodiment, marking device 20 may be configured in any size or shape to easily and cost effectively dispense liquid compound 30.

Liquid compound 30 is preferably colorless and invisible to the naked eye in visible wavelengths to allow for covert placement of liquid compound 30 on one or more target areas of one or more surfaces to be cleaned or disinfected. Liquid compound 30 dispensed on a surface will fluoresce or otherwise become visible in the presence of ultraviolet (UV) light, such as UV light emitted by light source 40.

In one embodiment, liquid compound 30 is an ink solution containing invisible pigments bound with, for example, an alcohol base, such as isopropyl alcohol, to allow for quick drying of liquid compound 30 once liquid compound 30 has been placed on one or more target areas of the one or more surfaces to be cleaned or disinfected. In one embodiment, liquid compound 30 dries in about 10 seconds or less after application onto a surface. Liquid compound 30 is preferably configured to leave an imperceptibly thin, invisible residue upon drying on any one of a variety of hard, substantially non-porous surfaces, such as countertops, faucets, toilet seats, floors, basins, doorknobs, workstations, keyboards, telephones, light switches, soap dispensers, and the like. Liquid compound 30 may also be non-contaminating and non-toxic, such that placement of liquid compound 30 on a surface does not create a health hazard to humans or animals.

Liquid compound 30 is readily and easily removable and washable, such that cleaning or wiping of the one or more surfaces to be cleaned or disinfected quickly and easily removes liquid compound 30. In one embodiment, liquid compound 30 is readily and easily removable by cleaning or wiping the one or more surfaces to be cleaned or disinfected using an aqueous solution, such as for example, soap and water. The physical properties of liquid compound 30, therefore, substantially differ from other, known compositions that are designed to be somewhat difficult to remove from a surface once applied thereon. An example of such other compositions include the invisible ink that might be applied to a ticket-holder's hand upon exiting, for example, a concert or an amusement park, to permit that person to return and re-enter the event the same day upon display of the ink as proof of prior admittance. In that case, the ink is necessarily of the type that is relatively difficult to remove; otherwise, simply washing one's hand may unintentionally remove the ink thereby frustrating the purpose for applying it to the person's hand in the first place.

Referring again to FIG. 1, light source 40 can be configured in the shape of a portable, handheld, flashlight-type light source, consisting of housing 42 having handle 44. Light source 40 may alternatively be configured in any shape or size to accommodate various portability, cost, and deployment considerations. In the embodiment of FIG. 1, housing 42 contains a power source, such as one or more batteries (not shown), one or more ultraviolet (UV) light emitters 45, such as one or more UV light emitting diodes (UV LEDs) 46 to which electricity flows from the power source, and a mechanism, such as switch 48, for controlling the flow of electricity between the power source and UV LEDs 46. UV LEDs 46 may vary in size and quantity depending on the size of light source 40 and the desired area of UV light to be emitted. In one embodiment, UV light emitters 45 emit light in a wavelength range of about 365-395 nm. One source of a suitable light source 40 is UltraViolet Distributing in Grayslake, Ill.

Figure 2:
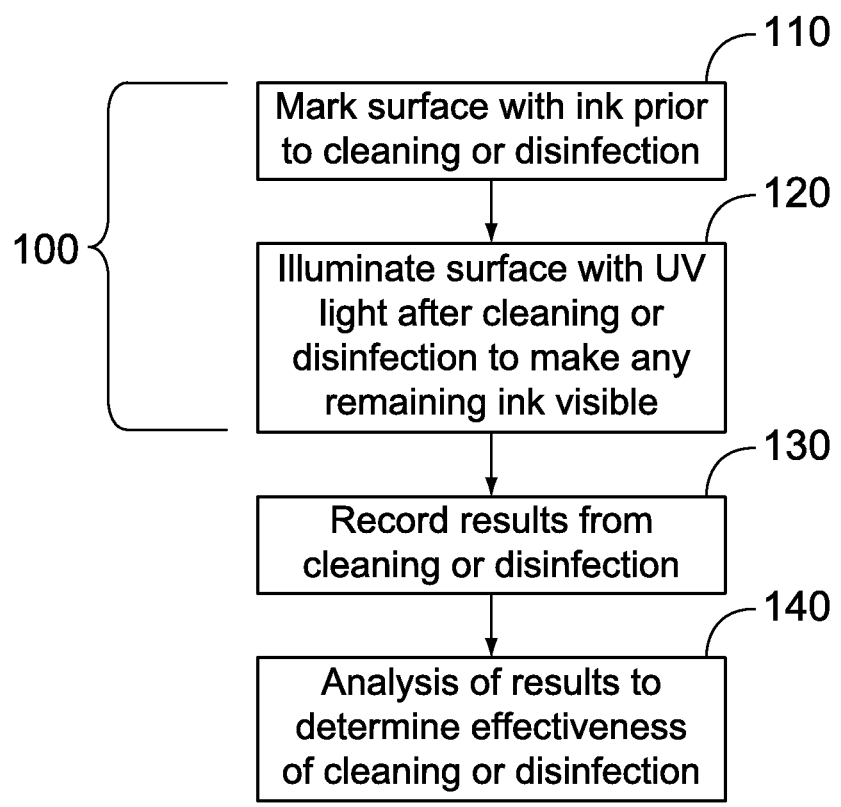
FIG. 2 is a flow chart showing a method of cleaning or disinfection verification in accordance with one embodiment of the present invention.

FIG. 2 depicts an exemplary cleaning and/or disinfection verification method 100. Method 100 may be employed in any location or area where verification of cleaning or disinfection of a particular surface or collection of surfaces is desired. The cleaning or disinfection process may be part of a formal cleaning procedure, for example, the terminal cleaning and disinfection of patient rooms upon discharge of the patient from the patient care facility or the cleaning of hotel rooms after guest checkout, or as part of any other cleaning practice of a public site. The one or more surfaces intended to be cleaned or disinfected may be cleaned or disinfected using, for example, soap and water, or organic or inorganic emulsifiers, detergents, abrasives, and chemical agents found in household or commercial disinfectants such as, for example, Simple Green, Glass Plus, Scrubbing Bubbles, or Ajax.

For example, a user may be the owner of an office building who wishes to ensure that the bathrooms located in the office building are thoroughly cleaned or disinfected by cleaning staff. The owner could apply method 100 to verify that surfaces in the bathroom have been properly cleaned or disinfected. In step 110 of method 100, a user covertly marks one or more target areas of one or more surfaces, such as one or more locations on a countertop, faucet, toilet seat, floor, basin, doorknob, workstation, keyboard, telephone, light switch, soap dispenser or the like, using tip 24 of marking device 20 to deposit liquid compound 30 on a surface intended to be cleaned or disinfected. To mark one or more target areas of one or more surfaces prior to cleaning or disinfection and inspection, tip 24 of marking device 20 is pressed to the one or more target areas to release ink from tip 24 onto the one or more surfaces.

In step 120, after the cleaning or disinfection process has purportedly been performed, a user using light source 40 may visually inspect the one or more surfaces by casting ultraviolet light upon the one or more surfaces previously marked using marking device 20 to detect any liquid compound 30 remaining on the surfaces that has not been removed as a result of the cleaning or disinfection process. When switch 48 is depressed to allow the flow of electricity, UV LEDs 46 emit UV light. When light source 40 emits UV light and illuminates a surface on which ink has been placed, any ink remaining on the surface will become visible under the UV light. As liquid compound 30 is easily and readily washable and removable from the one or more surfaces to be cleaned or disinfected using simple wiping gestures in connection with using, for example, soap and water or a common disinfectant, any remaining liquid compound 30 detected by visual inspection under ultraviolet light indicates that the one or more surfaces have not been completely and properly cleaned or disinfected. Alternatively, if the cleaning or disinfection of the one or more surfaces has been completely and properly performed as intended, liquid compound 30 would have been removed from all marked surfaces during the cleaning or disinfection process as nothing would fluoresce when illuminating the one or more surfaces using light source 40. A user can thus effortlessly and instantaneously verify proper cleaning or disinfection of marked surfaces upon illumination of the surfaces with UV light.

A user may optionally perform step 130 to record the results of cleaning or disinfection operations. For example, a user may perform steps 110 and 120 and record the results in step 130 to help determine the effectiveness and efficiency of cleaning procedures and cleaning personnel. In one embodiment, in connection with performing steps 110 and 120, data may be collected comprising a first status of the one or more target areas of the surface marked with ink prior to cleaning or disinfection, and a second status of the one or more target areas of the surface marked with ink following cleaning or disinfection operations of the one or more surfaces. The data may include, for example, an identification of which locations, rooms, surfaces, and target areas are marked and the status of the markings, including the presence or absence of liquid compound 30 and any qualitative and quantitative descriptions or measures of liquid compound 30, before and after cleaning or disinfection operations. As shown in step 140, the data may be analyzed to determine an effectiveness of cleaning or disinfection operations. Optionally, the data may be entered into a computer application program, such as a spreadsheet or other computer software capable of compiling, analyzing, and/or reporting the data. Such computer software may operate on a computer having a processor and memory, such as a personal computer, a handheld computing device, a smart phone, etc. Steps 130 and 140 may be integrated into a cleaning or disinfection procedure to develop improvements to the cleaning or disinfection procedures.

In an alternate embodiment, a user may use a recording device, such as a camera or camcorder or other imaging device capable of detecting liquid compound 30 applied to the one or more target areas of the one or more surfaces while exposed to UV light, to record the first status of the one or more target areas of the one or more surfaces marked with liquid compound 30 before, and/or the second status of the one or more target areas of the one or more surfaces marked with liquid compound 30 after, the cleaning or disinfection process. The recording device may wirelessly upload images in real-time or stream live video to one or more remote viewing devices, such as a computer monitor, television, or smart phone, for live viewing and/or recording of the status, including the presence or absence, of liquid compound 30 on the one or more target areas of the one or more surfaces before and after the cleaning or disinfection process of the one or more surfaces. In one embodiment, the recording device employs a Wi-Fi protocol coupled with the Internet to communicate the status. In another embodiment, the recording device uses a cellular communication channel to communicate the status. In yet another embodiment, the recording device uses the Bluetooth protocol to communicate the status. One of ordinary skill would recognize that any wireless method for communicating the status could be used in connection with the instant system.

While specific embodiments of the invention have been described in detail, it will be appreciated by those skilled in the art that various modifications and alternatives to those details could be developed in light of the overall teachings of the disclosure. Accordingly, the particular arrangements of the method and apparatus disclosed herein are meant to be illustrative only and not limiting as to the scope of the invention which is to be given the full breadth of the appended claims and any equivalents thereof.

What is claimed is:

1. A kit for cleaning or disinfection verification, comprising:
   a marking device comprising an ink solution that forms an invisible residue when applied to and allowed to dry on one or more surfaces intended to be cleaned or disinfected, the residue being invisible when exposed to light in a visible wavelength but which is made visible when exposed to light in an ultraviolet wavelength;

an ultraviolet light source for illuminating the invisible residue, if any, with ultraviolet light upon application of the ink solution to one or more surfaces intended to be cleaned or disinfected and following cleaning or disinfection operations of the one or more surfaces; and a recording device for recording a status of the one or more surfaces marked with the ink solution before and after the cleaning or disinfection process.

2. The kit of claim 1, wherein the recording device comprises an imaging system and a wireless communication system configured for wirelessly uploading images in real-time or streaming live video to one or more remote computers or devices.

3. A kit for cleaning or disinfection verification, comprising:

a portable, handheld marking device comprising a liquid compound that is invisible when exposed to light in a visible wavelength but which fluoresces when exposed to light in an ultraviolet wavelength;

a portable, handheld ultraviolet light emitting light source for illuminating the liquid compound, if any, with ultraviolet light upon application of the liquid compound to one or more substantially non-porous, inanimate surfaces intended to be cleaned or disinfected and following cleaning or disinfection operations of the one or more surfaces; and a recording device for recording a status of the one or more surfaces marked with the liquid compound before and after cleaning or disinfection operations.

4. The kit of claim 3, wherein the recording device comprises a wireless communication system for wirelessly communicating the status of the one or more surfaces to one or more remote devices.

5. A method of verifying cleaning or disinfection, comprising the steps of:

marking one or more surfaces intended to be cleaned or disinfected with an ink that is invisible when exposed to light in a visible wavelength but which is made visible when exposed to light in an ultraviolet wavelength, the ink forming an imperceptibly thin and invisible residue on the one or more surfaces when dry and is readily and easily removable by cleaning or wiping the one or more surfaces using an aqueous solution;

recording a first status of the one or more surfaces before cleaning or disinfection operations;

visually inspecting the one or more surfaces for the presence or absence of the ink, comprising illuminating the one or more surfaces with ultraviolet light to make visible any ink remaining on the one or more surfaces after cleaning or disinfection operations have been performed;

recording a second status of the one or more surfaces after the cleaning or disinfection operations; and analyzing the first and second status of the one or more surfaces to determine an effectiveness of the cleaning or disinfection operations.

6. The method of claim 5, further comprising the step of wirelessly communicating the first and second status to one or more remote computers.

7. A method of verifying cleaning or disinfection, comprising the steps of:

marking one or more target areas of a surface with ink that is invisible when exposed to light in a visible wavelength but which fluoresces when exposed to light in an ultraviolet wavelength;

recording a first status of the one or more target areas of the surface marked with the ink prior to cleaning or disinfection operations of the surface;

following cleaning or disinfection operations of the surface, determining the presence or absence of the ink, comprising illuminating the one or more target areas of the surface with ultraviolet light after cleaning or disinfection operations to cause any ink remaining on one or more target areas of the surface after the cleaning or disinfection operations to fluoresce;

recording a second status of the one or more target areas of the surface marked with the ink following cleaning or disinfection operations of the surface;

analyzing an effectiveness of the cleaning or disinfection operations of the surface, comprising comparing the one or more target areas for ink before and after the cleaning or disinfection operations.

8. The method of claim 7, wherein the step of recording the first and second status comprises wirelessly communicating images or video to one or more remote computers.

* * * * *